US012670974B2

(12) United States Patent
     Shah

(10) Patent No.:  US 12,670,974 B2
(45) Date of Patent:      Jun. 30, 2026

(54) GENERATING NOTES USING MACHINE LEARNING

(71) Applicant: Birth Model, Inc., Fort Lee, NJ (US)

(72) Inventor: Anish J. Shah, Fort Lee, NJ (US)

(73) Assignee: Birth Model, Inc., Fort Lee, NJ (US)

( * ) Notice: Subject to any disclaimer, the term of this patent is extended or adjusted under 35 U.S.C. 154(b) by 10 days.

(21) Appl. No.: 18/680,780

(22) Filed: May 31, 2024

(65) Prior Publication Data

US 2025/0372213 A1     Dec. 4, 2025

(51) Int. Cl.
| | |
|---|---|
| *G16H 10/60* | (2018.01) |
| *A61B 5/00* | (2006.01) |
| *G06F 40/284* | (2020.01) |
| *G16H 15/00* | (2018.01) |
| *G16H 20/10* | (2018.01) |

(52) U.S. Cl.
CPC ........... *G16H 10/60* (2018.01); *A61B 5/0011* (2013.01); *G06F 40/284* (2020.01); *G16H 15/00* (2018.01); *G16H 20/10* (2018.01)

(58) Field of Classification Search
CPC ... A61B 5/0015; A61B 5/0024; A61B 5/0026; A61B 5/0028; A61B 5/0205; A61B 5/02438; A61B 5/0011; A61B 5/327; A61B 5/7267; A61B 8/06; A61B 8/0883; A61B 8/12; A61B 8/4416; A61B 8/488; A61B 8/5215
See application file for complete search history.

(56) References Cited

U.S. PATENT DOCUMENTS

| | | | | |
|---|---|---|---|---|
| 7,860,903 | B2 * | 12/2010 | Shah ..................... | G06F 16/86 |
| | | | | 707/810 |
| 2008/0091733 | A1 * | 4/2008 | Shelton ................ | G06F 16/242 |
| 2011/0196704 | A1 * | 8/2011 | Mansour ............... | G16H 10/60 |
| | | | | 707/723 |

(Continued)

FOREIGN PATENT DOCUMENTS

| | | | | |
|---|---|---|---|---|
| WO | WO-2023175089 A1 * | 9/2023 | ......... | G06F 16/3329 |
| WO | WO-2024058826 A1 * | 3/2024 | ............. | A61B 6/107 |

OTHER PUBLICATIONS

Keszthelyi D, Gaudet-Blavignac C, Bjelogrlic M, Lovis C. Patient Information Summarization in Clinical Settings: Scoping Review. JMIR Med Inform. Nov. 28, 2023;11:e44639. doi: 10.2196/44639 (Year: 2023).*

(Continued)

*Primary Examiner* — Rachel L. Porter
(74) *Attorney, Agent, or Firm* — Fish & Richardson P.C.

(57)     ABSTRACT

Methods, systems, and apparatus, including computer programs encoded on a computer storage medium, for generating a note for a subject. In one aspect, a method comprises: obtaining a note template that defines a format of a note for a subject; automatically querying one or more record databases to obtain a set of electronic record data for the subject; generating a model input to a generative machine learning model based at least in part on: (i) the note template, and (ii) the set of electronic record data for the subject; processing the model input using the generative machine learning model and in accordance with values of a set of generative machine learning model parameters to generate a model output that defines the note for the subject; and outputting the note for the subject.

24 Claims, 7 Drawing Sheets

CLINICAL NOTE GENERATION SYSTEM 100

(56)     References Cited

U.S. PATENT DOCUMENTS

| | | | |
|---|---|---|---|
| 2013/0167111 A1* | 6/2013 | Moore | H04L 67/10 |
| | | | 717/105 |
| 2017/0196497 A1* | 7/2017 | Ray | G06N 7/01 |
| 2020/0126663 A1* | 4/2020 | Lucas | G06V 30/19013 |
| 2021/0125721 A1* | 4/2021 | Kemp | G16H 10/60 |
| 2022/0133166 A1* | 5/2022 | Ghodsian | A61B 5/435 |
| | | | 600/304 |
| 2023/0104655 A1* | 4/2023 | Amarasingham | G16H 15/00 |
| | | | 705/2 |
| 2024/0029901 A1* | 1/2024 | Ezhov | G16H 10/60 |

OTHER PUBLICATIONS

Vaswani et al., "Attention is all you need," 31st Conference on Neural Information Processing Systems, published on Aug. 2, 2023, arXiv:1706.03762, 15 pages.

* cited by examiner

CLINICAL NOTE GENERATION SYSTEM 100

AUTOMATED GENERATION OF A CLINICAL NOTE FOR A PATIENT

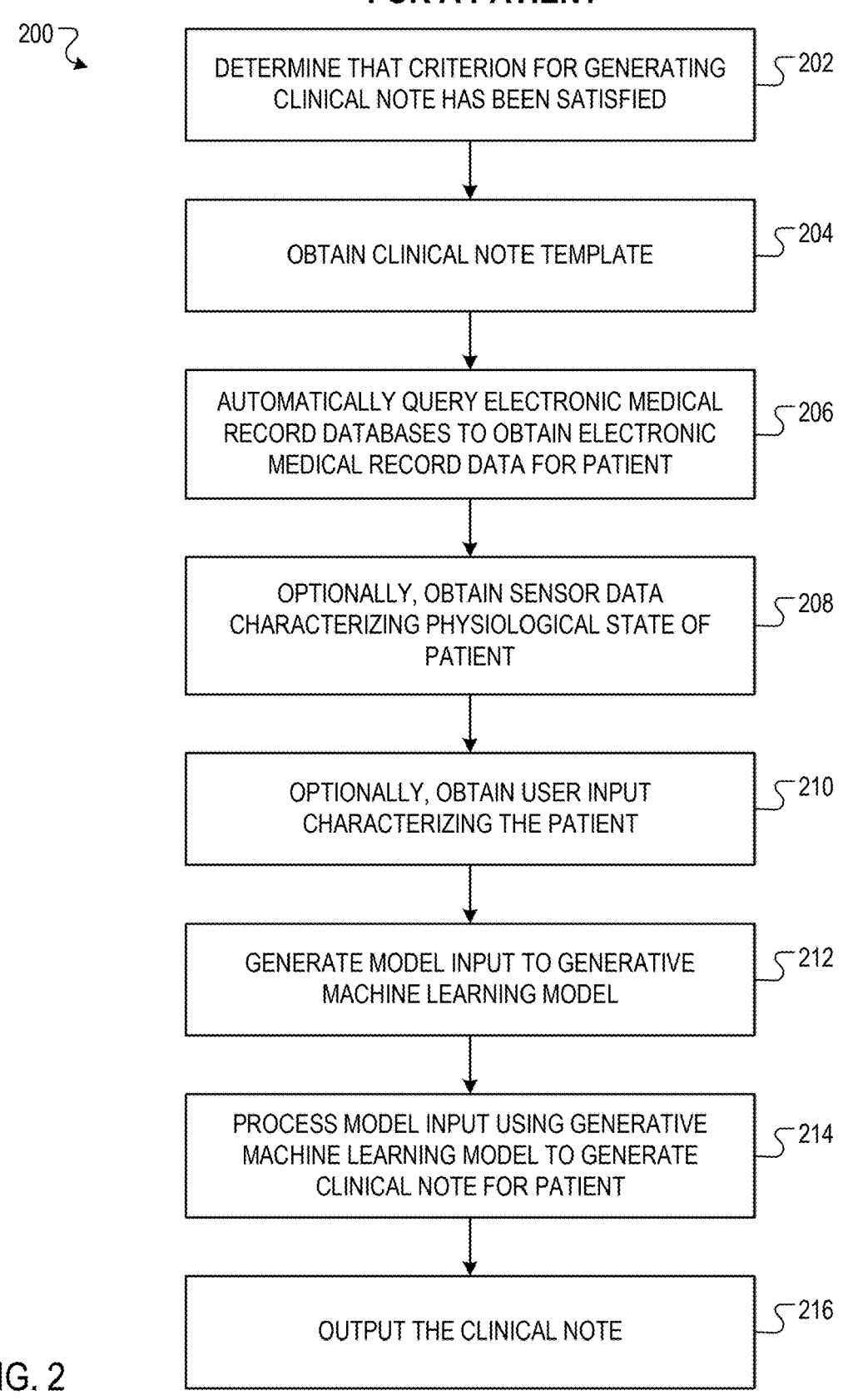

200

DETERMINE THAT CRITERION FOR GENERATING CLINICAL NOTE HAS BEEN SATISFIED ⌇202

OBTAIN CLINICAL NOTE TEMPLATE ⌇204

AUTOMATICALLY QUERY ELECTRONIC MEDICAL RECORD DATABASES TO OBTAIN ELECTRONIC MEDICAL RECORD DATA FOR PATIENT ⌇206

OPTIONALLY, OBTAIN SENSOR DATA CHARACTERIZING PHYSIOLOGICAL STATE OF PATIENT ⌇208

OPTIONALLY, OBTAIN USER INPUT CHARACTERIZING THE PATIENT ⌇210

GENERATE MODEL INPUT TO GENERATIVE MACHINE LEARNING MODEL ⌇212

PROCESS MODEL INPUT USING GENERATIVE MACHINE LEARNING MODEL TO GENERATE CLINICAL NOTE FOR PATIENT ⌇214

OUTPUT THE CLINICAL NOTE ⌇216

FIG. 2

GENERATING A MODEL INPUT TO A GENERATIVE
MACHINE LEARNING MODEL

300

RESOLVE INCONSISTENCIES IN ELECTRONIC
MEDICAL RECORD DATA FOR PATIENT                302

PROCESS ELECTRONIC MEDICAL RECORD DATA TO
IDENTIFY MEDICAL CLASSIFICATION CODES THAT
APPLY TO PATIENT                              304

PROCESS SENSOR DATA TO GENERATE SENSOR
DATA FEATURES                                306

GENERATE MODEL INPUT TO GENERATIVE
MACHINE LEARNING MODEL                       308

GENERATING NEW CLINICAL NOTES BASED ON CONTINUOUS MONITORING OF SENSOR DATA

ADAPTIVELY UPDATING A CLINICAL NOTE BASED ON USER FEEDBACK

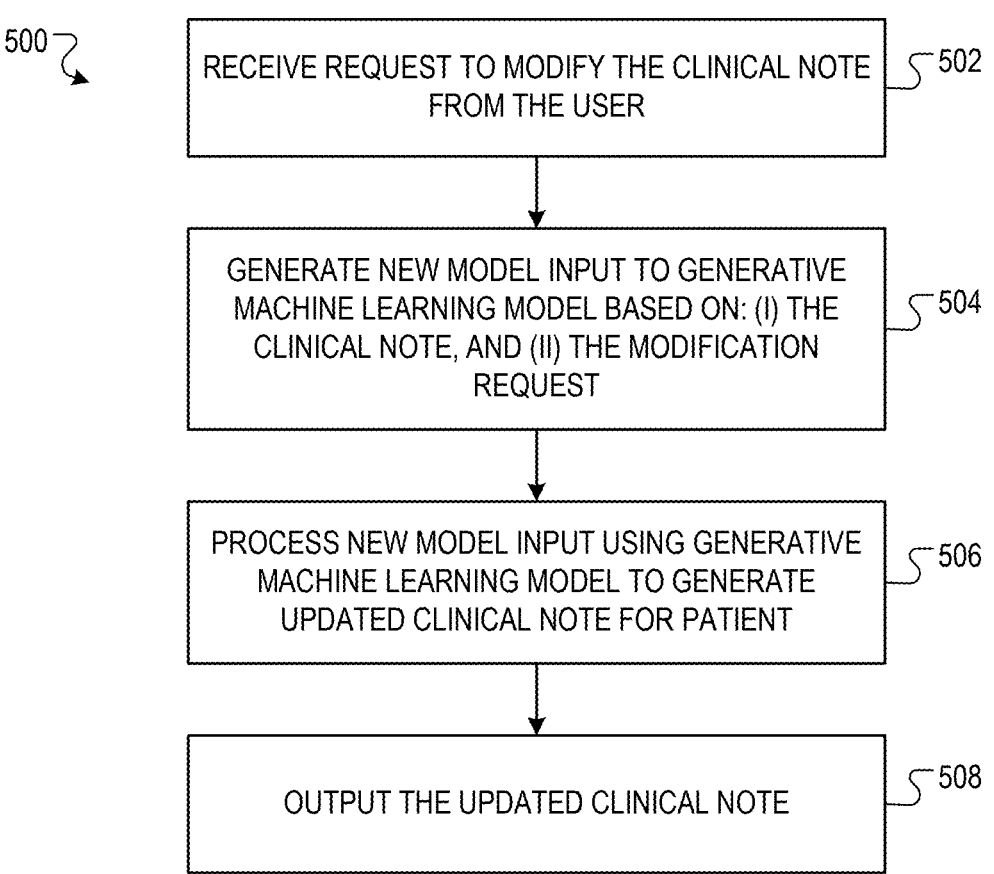

500

RECEIVE REQUEST TO MODIFY THE CLINICAL NOTE FROM THE USER ⟍502

GENERATE NEW MODEL INPUT TO GENERATIVE MACHINE LEARNING MODEL BASED ON: (I) THE CLINICAL NOTE, AND (II) THE MODIFICATION REQUEST ⟍504

PROCESS NEW MODEL INPUT USING GENERATIVE MACHINE LEARNING MODEL TO GENERATE UPDATED CLINICAL NOTE FOR PATIENT ⟍506

OUTPUT THE UPDATED CLINICAL NOTE ⟍508

FIG. 5

GENERATING A CLINICAL NOTE USING A
GENERATIVE MACHINE LEARNING MODEL

**TRAINING A GENERATIVE MACHINE LEARNING
MODEL USED FOR CLINICAL NOTE GENERATION**

700

OBTAIN TRAINING DATA FOR TRAINING
GENERATIVE MACHINE LEARNING MODEL    702

TRAIN GENERATIVE MACHINE LEARNING MODEL ON
THE TRAINING DATA TO PERFORM A LANGUAGE
MODELING TASK    704

GENERATING NOTES USING MACHINE LEARNING

BACKGROUND

This specification relates to processing data using machine learning models.

Machine learning models receive an input and generate an output, e.g., a predicted output, based on the received input. Some machine learning models are parametric models and generate the output based on the received input and on values of the parameters of the model.

Some machine learning models are deep models that employ multiple layers of models to generate an output for a received input. For example, a deep neural network is a deep machine learning model that includes an output layer and one or more hidden layers that each apply a non-linear transformation to a received input to generate an output.

SUMMARY

This specification describes a system implemented as computer programs on one or more computers in one or more locations that can generate a clinical note for a patient using a generative machine learning model.

Throughout this specification, a "patient" can refer to a human subject, e.g., that is receiving healthcare services.

Throughout this specification, a "clinical note" can refer to a textual record that describes healthcare services provided to a patient. For instance, a clinical note can be an operative note, or a progress note, or a delivery note.

Throughout this specification, an "operative note" can refer to a clinical note that describes a surgical procedure performed on a patient, and can include one or more of: patient identification information; data and time of surgery; preoperative diagnosis; name of the health care provider that performed the procedure; description of the surgical procedure performed; anesthesia used; detailed account of the surgical steps, e.g., incision, procedure, and closure; complications (if any); estimated blood loss; and so forth.

Throughout this specification, a "progress note" can refer to a clinical note that describes the status of a patient and ongoing care being provided to the patient, and can include one or more of: patient identification information; data and time of the note; subjective information, e.g., patient complaints or symptoms in their own words; objective information, e.g., clinical findings such as vital signs, physical examination results, and lab results; assessment, e.g., an interpretation of the subjective and objective data by a healthcare provider; treatment plans, e.g., any new tests, medications, or interventions; and so forth.

Throughout this specification, a "delivery note" can refer to a clinical note that describes a childbirth process of a patient, and can include one or more of: patient identification information; date and time of delivery; type of delivery, e.g., vaginal birth or cesarean section; details of labor, e.g., onset, duration, stages, and interventions; condition of the patient and the baby at the time of delivery; Apgar scores of the baby; complications during labor and delivery (if any); anesthesia or analgesia used (if any); and so forth.

According to a first aspect, there is provided a method performed by one or more computers, the method comprising: obtaining a clinical note template that defines a format of a clinical note for a patient; automatically querying one or more electronic medical record databases to obtain a set of electronic medical record data for the patient; generating a model input to a generative machine learning model based at least in part on: (i) the clinical note template, and (ii) the set of electronic medical record data for the patient; processing the model input using the generative machine learning model and in accordance with values of a set of generative machine learning model parameters to generate a model output that defines the clinical note for the patient; and outputting the clinical note for the patient.

In some implementations, generating the model input to the generative machine learning model comprises: processing the set of electronic medical record data for the patient to classify, for each medical classification code in a predefined set of possible medical classification codes, whether the medical classification code applies to the patient; identifying that one or more medical classification codes from the predefined set of possible medical classification codes apply to the patient; and in response, including the one or more medical classification codes that apply to the patient in the model input to the generative machine learning model.

In some implementations, processing the set of electronic medical record data for the patient to classify, for each medical classification code in the predefined set of possible medical classification codes, where the medical classification code applies to the patient comprises, for each medical classification code in the predefined set of possible medical classification codes: determining whether the medical classification code applies to the patient by evaluating whether the set of electronic medical record data for the patient satisfies one or more criteria associated with the medical classification code.

In some implementations, generating the model input to the generative machine learning model comprises: obtaining sensor data that is generated by a sensor that is on or in proximity to the patient and that characterizes a physiological state of the patient; processing the sensor data to derive one or more features of the sensor data; and including the one or more features derived from the sensor data in the model input to the generate machine learning model.

In some implementations, the sensor data comprises respective fetal heart rate data for one or more fetuses of the patient.

In some implementations, the sensor data comprises dilation data that defines an amount of dilation of a cervix of the patient.

In some implementations, the sensor data comprises drug dosage data that characterizes an amount of a drug being administered to the patient.

In some implementations, generating the model input to the generative machine learning model comprises: determining, for one or more fields in the electronic medical record data for the patient, that the electronic medical record includes a plurality of distinct entries for the field; and providing, by a user interface, an option to select one of the plurality of distinct entries for the field; and receiving, from by way of the user interface, selection data that selects one of the plurality of distinct entries for the field; and including only the selected entry for the field in the model input to the generative machine learning model.

In some implementations, the method further comprises, after providing the clinical note for the patient: receiving, by a user interface, a request to modify the clinical note for the patient; generating a new model input to the generative machine learning model that comprises at least: (i) the clinical note for the patient, and (ii) data defining the request to modify the clinical note for the patient; and processing the new model input using the generative machine learning model to generate a new clinical note for the patient that reflects the request to modify the clinical note for the patient.

In some implementations, outputting the clinical note for the patient comprises presenting the clinical note on a display of a device.

In some implementations, the method further comprises: continuously and automatically monitoring sensor data generated by one or more sensors that are on or in proximity to the patient and that characterize a physiological state of the patient; and determining, based on the continuous and automated monitoring of the sensor data generated by the one or more sensors, that a criterion for generating a clinical note for the patient has been satisfied; and in response, generating the clinical note for the patient.

In some implementations, determining, based on the continuous and automated monitoring of the sensor data generated by the one or more sensors, that the criterion for generating the clinical note for the patient has been satisfied comprises: processing current sensor data for the patient to generate a current feature of the current sensor data; and determining that the criterion for generating the clinical note for the patient has been satisfied based on the current feature of the current sensor data.

In some implementations, the model input to the generative machine learning model comprises a concatenation of: (i) the clinical note template, and (ii) the set of electronic medical record data for the patient.

In some implementations, the generative machine learning model has been trained by a machine learning training technique to perform a language modeling task.

In some implementations, the model output that defines the clinical note for the patient comprises a sequence of textual tokens; and processing the model input using the generative machine learning model and in accordance with values of the set of generative machine learning model parameters to generate the model output that defines the clinical note for the patient comprises, for each of a plurality of positions in the sequence of textual tokens: processing: (i) the model input, and (ii) any textual tokens at preceding positions that precede the position in the sequence of textual tokens, using the generative machine learning model to generate a score distribution over a set of possible textual tokens; and selecting a textual token to occupy the position in the sequence of textual tokens using the score distribution over the set of possible textual tokens.

In some implementations, selecting a textual token to occupy the position in the sequence of textual tokens using the score distribution over the set of possible textual tokens comprises selecting a textual token having a highest score under the score distribution over the set of possible textual tokens as the textual token to occupy the position in the sequence of textual tokens.

In some implementations, the set of electronic medical record data for the patient comprises one or more previous clinical notes for the patient.

In some implementations, the clinical note template comprises a sequence of text, wherein the sequence of text comprises a plurality of wildcard fields that are each designated to be replaced with a corresponding type of information related to the patient.

In some implementations, obtaining the clinical note template comprises: providing, by a user interface, a plurality of possible clinical note templates; and receiving, from a user, a selection that identifies the clinical note template from among the plurality of possible clinical note templates.

In some implementations, the clinical note is an operative note that describes a surgery performed on the patient.

In some implementations, the clinical note is a delivery note that describes a childbirth process for the patient.

In some implementations, the clinical note is a progress note that describes a status of the patient and ongoing care being provided to the patient.

According to another aspect, there is provided a system comprising: one or more computers; and one or more storage devices communicatively coupled to the one or more computers, wherein the one or more storage devices store instructions that, when executed by the one or more computers, cause the one or more computers to perform operations of the methods described herein.

According to another aspect there are provided one or more non-transitory computer storage media storing instructions that when executed by one or more computers cause the one or more computers to perform operations of the methods described herein.

Particular embodiments of the subject matter described in this specification can be implemented so as to realize one or more of the following advantages.

Recording accurate and detailed clinical notes is crucial for enabling healthcare providers involved in patient care to have access to comprehensive and up-to-date information, which can facilitate informed medical decision making, reduce the risk of medical errors, and increase the quality of medical care. Healthcare providers often manually create clinical notes, e.g., by dictation or by manual data entry by way of a keyboard. However, the manual approach for generating clinical notes tends to be time consuming, e.g., because healthcare providers may be required to generate large numbers (e.g., dozens) of clinical notes each day, and error prone, e.g., because healthcare providers may be required to manually access and retrieve relevant patient information from electronic medical record databases by processes that introduce many opportunities for human error.

One approach to streamlining the generation of clinical notes may involve the creation of a set of clinical note templates. Each clinical note template can define a standardized framework for documenting healthcare services provided to a patient, and can include a sequence of text with one or more "wildcard fields" that are each designated to be replaced with a corresponding type of information related to the patient. When tasked with the creation of a new clinical note, a healthcare provider can select an available clinical note template to use as a starting point for a new clinical note. However, this approach may only partially and incompletely address the issues that arise in fully manual clinical note generation. For instance, clinical note templates may be overly rigid in nature and time consuming to manually adapt to the large number of highly diverse and individualized scenarios that arise when providing medical care. Further, significant opportunity for human error remains as healthcare providers manually populate the wildcard fields of a clinical note template with data retrieved from electronic medical records.

The clinical note generation system described in this specification addresses these issues. More specifically, to generate a clinical note for a patient, the system can obtain a clinical note template and can automatically query one or more electronic medical record databases to obtain a set of electronic medical record data for the patient. The system can generate a model input to a generative machine learning model using the clinical note template and the electronic medical record data, e.g., by serializing the clinical note template and the electronic medical record data into a sequence of tokens, e.g., where each token is drawn from a set of possible tokens that includes one or more of: characters, numbers, word pieces, words, and so forth. The system can then process the model input using the generative machine learning model to generate a model output that defines the clinical note for the patient. The generative machine learning model can be a foundation model, e.g., that is trained to perform a language modeling task, and can flexibly integrate the electronic medical record data for the patient into the clinical note template and adaptively modify the clinical template as needed to reflect the particulars of the medical care provided to the patient. The system can thus generate clinical notes rapidly, e.g., by leveraging clinical note templates and a generative machine learning model, and accurately, e.g., by using electronic medical record data automatically retrieved from electronic medical record databases.

Including the clinical note template in the model input to the generative machine learning model can allow the generative machine learning model to have a less complex architecture and to be trained on less training data than would otherwise be required, thus enabling reduced consumption of computational resources (e.g., memory and computing power) during training and during inference. More specifically, absent the inclusion of the clinical note template in the model input, the generative machine learning model would be required to implicitly derive the appropriate format and structure for the clinical note based on information encoded in the parameter values of the generative machine learning model during training. Encoding sufficient information in the parameters of the generative machine learning model to enable the generation of high quality clinical notes may thus require greater quantities of training data and a more complex architecture (e.g., with more parameters) than are required by a generative machine learning model that receives a clinical note template as part of the model input.

As part of generating the model input to the generative machine learning model, the system can process electronic medical record data for the patient to classify, for each medical classification code in a predefined set of possible medical classification codes, whether the medical classification code applies to the patient. The system can then include medical classification codes that apply to the patient in the model input to the generative machine learning model. The inclusion of the medical classification codes in the model input to the generative machine learning model can increase the quality of the generated clinical note, as the generative machine learning model can adaptively generate the clinical note in a manner that incorporates the medical classification code.

Further, including the medical classification codes in the model input to the generative machine learning model can allow the generative machine learning model to have a less complex architecture and to be trained on less training data than would otherwise be required, thus enabling reduced consumption of computational resources (e.g., memory and computing power) during training and during inference. More specifically, absent the inclusion of the medical classification codes in the model input, the generative machine learning model would be required to implicitly identify and generate appropriate medical classification codes based on information encoded in the parameter values of the generative machine learning model during training. Encoding sufficient information in the parameters of the generative machine learning model to enable the generation of clinical notes that incorporate medical classification codes may thus require greater quantities of training data and a more complex architecture (e.g., with more parameters) than are required by a generative machine learning model that receives the medical classification codes as part of the model input. Put another way, the system can reduce the required complexity of the generative machine learning model by leveraging domain-specific criteria for generating medical classification codes as a pre-processing step in generating the model input to the generative machine learning model.

As part of generating the model input to the generative machine learning model, the system can process sensor data (e.g., generated by a fetal heart rate sensor, or a dilation sensor, or a drug dosage sensor, or a vital sign sensor) to generate features of the sensor data, e.g., using signal processing and/or machine learning operations. The system can then include the sensor data features in the model input to the generative machine learning model. The inclusion of the sensor data features in the model input to the generative machine learning model can increase the quality of the generated clinical note, as the generative machine learning model can adaptively generate the clinical note in a manner that incorporates the sensor data features.

Further, including the sensor data features in the model input to the generative machine learning model can allow the generative machine learning model to have a less complex architecture and to be trained on less training data than would otherwise be required, thus enabling reduced consumption of computational resources (e.g., memory and computing power) during training and during inference. More specifically, absent the inclusion of the sensor data features in the model input, the generative machine learning model would be required to process raw sensor data to implicitly identify and generate appropriate sensor data features based on information encoded in the parameter values of the generative machine learning model during training. Encoding sufficient information in the parameters of the generative machine learning model to enable the generation of clinical notes that incorporate sensor data features may thus require greater quantities of training data and a more complex architecture (e.g., with more parameters) than are required by a generative machine learning model that receives the sensor data features as part of the model input. Put another way, the system can reduce the required complexity of the generative machine learning model by leveraging domain-specific criteria for generating sensor data features as a pre-processing step in generating the model input to the generative machine learning model.

The details of one or more embodiments of the subject matter of this specification are set forth in the accompanying drawings and the description below. Other features, aspects, and advantages of the subject matter will become apparent from the description, the drawings, and the claims.

BRIEF DESCRIPTION OF THE DRAWINGS

FIG. 2 is a flow diagram of an example process for generating a clinical note for a patient.

FIG. 5 is a flow diagram of an example process for adaptively updating a clinical note generated by a generative machine learning model based on user feedback.

Like reference numbers and designations in the various drawings indicate like elements.

DETAILED DESCRIPTION

Figure 1:
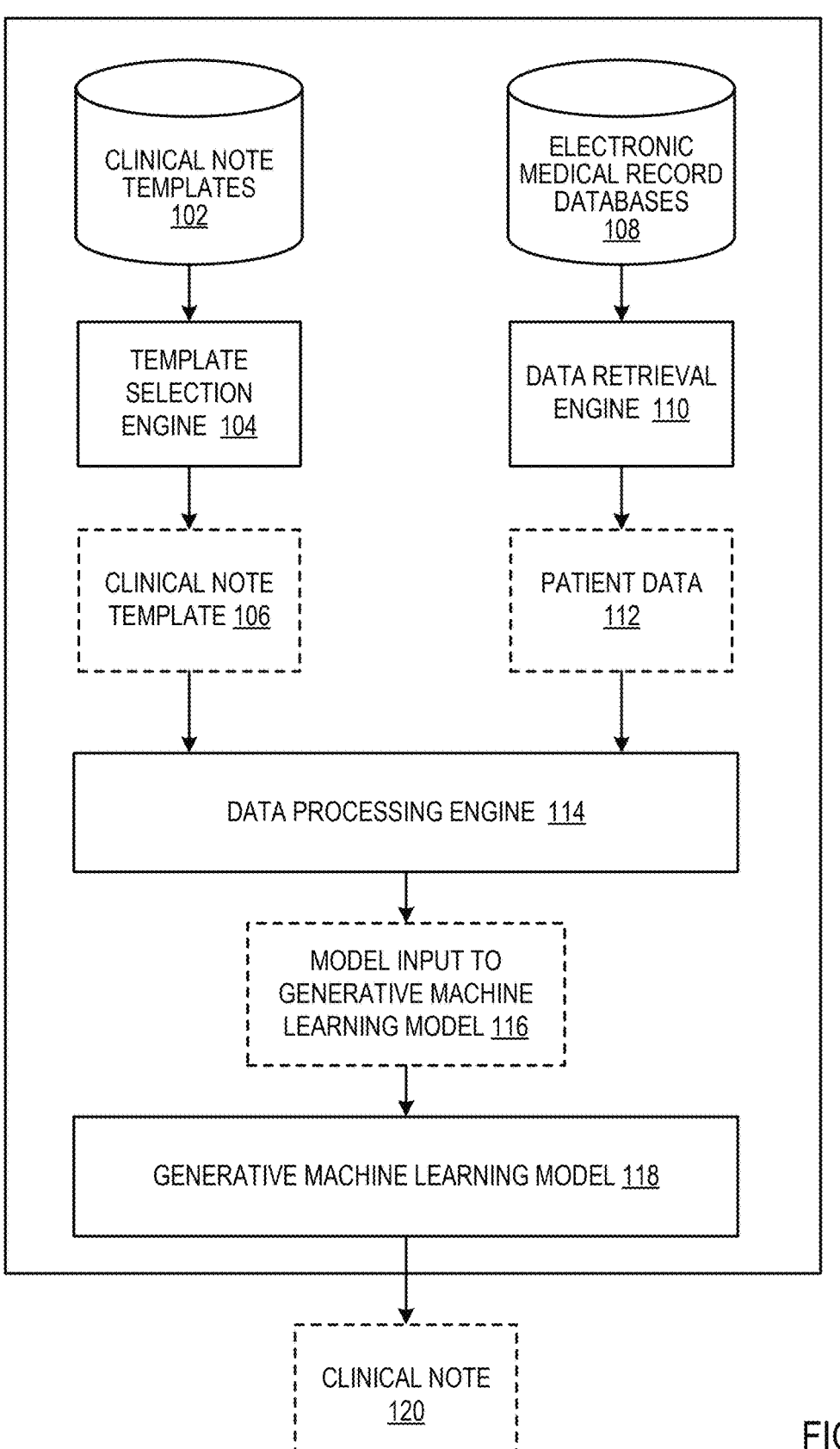
FIG. 1 shows an example clinical note generation system.

FIG. 1 shows an example clinical note generation system 100. The clinical note generation system 100 is an example of a system implemented as computer programs on one or more computers in one or more locations in which the systems, components, and techniques described below are implemented.

The clinical note generation system 100 is configured to generate a clinical note 120 for a patient. The clinical note 120 can be, e.g., an operative note (that describes a surgical procedure performed on the patient), or a progress note (that describes the status of the patient and ongoing care being provided to the patient), or a delivery note (that describes a childbirth process for the patient). The clinical note can have any appropriate length, e.g., at least 50 words, or at least 100 words, or at least 200 words.

The system 100 can generate a clinical note 120 for a patient in response to determining that criteria for generating a new clinical note 120 for the patient have been satisfied.

For instance, the system 100 can generate a clinical note 120 in response to receiving a request to generate a clinical note from a user of the system 100, e.g., a healthcare provider for the patient. In more detail, the user can interact with a user interface (e.g., a graphical user interface (GUI)) made available by the system 100 to request the generation of a new clinical note for the patient, e.g., by selecting an interactive graphical user interface element (e.g., button) that triggers the generation of a new clinical note. The system 100 can cause the user interface to be rendered on a display of a user device of the user. The user device can be, e.g., a smartphone, or a tablet, or a personal computer.

As another example, the system 100 can perform continuous and automated monitoring of sensor data characterizing the physiological state of the patient, and can determine that a criterion for generating a new clinical note 120 for the patient has been satisfied based on the monitoring of the sensor data. Example techniques for determining that a criterion for generating a new clinical note for a patient has been satisfied based on monitoring of real-time sensor data are described in more detail below with reference to FIG. 4.

The system 100 includes a set of clinical note templates 102, a template selection engine 104, one or more electronic medical record databases 108, a data retrieval engine 110, a data processing engine 114, and a generative machine learning model 118, which are each described next (and throughout this specification).

Each clinical note template in the set of clinical note templates 102 defines a standardized framework for documenting healthcare services provided to a patient. A clinical note template includes a sequence of text with one or more "wildcard fields" that are each designated to be replaced with a corresponding type of information related to the patient. Each wildcard field can be demarcated by specific characters, e.g., with "[" designating the start of a wildcard field and "]" designating the end of a wildcard field. Each wildcard field can include text that defines the type of information to be substituted into the wildcard field, e.g., "age", "first_name", "last_name", "gender_of_baby", and so forth.

The set of clinical note templates 102 can include clinical note templates corresponding to different types of clinical notes, e.g., operative notes, progress notes, or delivery notes. The set of clinical note templates 102 can further include multiple variations of a single type of clinical note, e.g., corresponding to variations of the type of clinical note that most commonly occur in practice.

The set of clinical note templates 102 can include any appropriate number of clinical note templates, e.g., at least 5, or at least 10, or at least 50 clinical note templates. The set of clinical note templates 102 can include clinical note templates that are manually generated by users, or clinical note templates that are generated by an automated procedure (e.g., as an output of a generative machine learning model), or both. The system 100 can be "pre-loaded" with default clinical note templates, and can enable users to add new clinical note templates when desired. The system 100 can maintain a user-specific sets of clinical note templates, i.e., such that each user of the system 100 can have a customized set of clinical note templates 102 that are specific to that user.

A few examples of possible clinical note templates are provided next for illustrative purposes. In each of these examples, wildcard fields are delimited by square brackets: "[" and "]".

Example template clinical note #1, for multiple infants delivered by cesarean section: "[Patient's First Name] [Patient's Last Name], a [Patient's Age]-year-old with gestation age [Gestational Age Weeks]+[Gestational Age Days] weeks underwent a [Primary/Repeat] [Delivery Method] of twins. The time from rupture of membranes to delivery was [Time from Rupture of Membranes to Delivery]. The amniotic fluid was noted to be clear, and the placenta exhibited normal discoid shape. The uterine incision was made as a [Type of Uterine Incision], and delivery of the fetus proceeded uneventfully. The first was a [Infant #1 Gender] neonate, weighing [Infant #1 Birth Weight] grams, and was delivered without complications in [Cephalic/Breech of #1 Infant] presentation. The Apgar scores were [Infant #1 1 min Apgar Score] at 1 minute and [Infant #1 5 min Apgar Score] at 5 minutes post-delivery. The second was a [Infant #2 Gender] neonate, weighing [Infant #2 Birth Weight] grams, and was delivered without complications in [Cephalic/Breech of #2 Infant] presentation. The Apgar scores were [Infant #2 1 min Apgar Score] at 1 minute and [Infant #2 5 min Apgar Score] at 5 minutes post-delivery. Both ovaries and bilateral fallopian tubes were normal appearing."

"Example template clinical note #2, for operative delivery of twins: [Patient's First Name] [Patient's Last Name], a [Patient's Age]-year-old with gestation age [Gestational Age Weeks]+[Gestational Age Days] weeks underwent a [Operative Delivery Type]-assisted [Delivery Method] of twins. Due to poor maternal effort and nonreassuring fetal heart tracing, the patient was counseled regarding all risks, benefits and alternatives. The first infant's fetal station was +2. The NICU team was called to the room. Consents had been signed. The time from rupture of membranes to delivery was [Time from Rupture of Membranes to Delivery]."

Example template clinical note #3, for normal spontaneous vaginal delivery or vaginal birth after cesarean: "On [actual_delivery_time], [first_name] [last_name], a [Patient's Age]-year-old with gestation age [gestational_age_weeks]+[gestational_age_days] weeks, underwent a [delivery_sub_method–if applicable] [delivery_method].

The time from rupture of membranes to delivery was [time from rupture of membranes to delivery]. Patient was fully dilated for [Time from Fully Dilated to Delivery]."

The template selection engine 104 is configured to enable the selection of a particular clinical note template 106 from the set of clinical note templates 102, e.g., for use in generating the clinical note 120 for the patient. The template selection engine 104 can enable the selection of a clinical note template 106, e.g., by providing a representation of some or all of the clinical note templates in the set of clinical note templates 102 to a user by way of a user interface. For instance, in response to a user interacting with the user interface to request the generation of a new clinical note for a patient, the system 100 can present a list of available clinical note templates to the user. The user can then select an appropriate clinical note template from among the clinical note templates presented by the system on the user interface.

In some cases, the template selection engine 104 can select a clinical note template 106 from the set of clinical note templates 102 in an automated fashion, i.e., without explicit user input, in accordance with one or more predefined rules. For instance, if the system 100 initiates the generation of a new clinical note based on continuous and automated monitoring of real-time sensor data characterizing the patient, as will be described in more detail below, then the system can select a default progress note template as the clinical note template to be used in generating the output clinical note 120.

The one or more electronic medical record databases 108 can be any appropriate data repositories that store medical information related to patients, e.g., including one or more of: medical history, diagnoses, treatments, medications, laboratory results, sensor data generated by sensors located on or in proximity to patients, clinical notes, and so forth. An electronic medical record database can have an associated application programming interface (API) that enables automated querying of patient information from the electronic medical record database, and automated storage of new or updated patient information in the electronic medical record database. Patient medical information stored in electronic medical record databases can be dynamically updated over time, e.g., as healthcare providers enter new data during patient visits, or as data from medical devices and sensors is uploaded through integration interfaces, or as results from laboratory tests or diagnostic imaging are electronically transmitted to the one or more electronic medical record databases.

The data retrieval engine 110 is configured to automatically query the one or more electronic medical record databases 108 to obtain patient data 112 characterizing the patient, in particular, where the patient data 112 includes a set of electronic medical record data for the patient. The data retrieval engine 110 can be remotely located from the electronic medical record databases 108, and can transmit data to and receive data from the electronic medical record databases 108 by way of a data communications network, e.g., a local area network (LAN), a wide area network (WAN), or the internet. In particular, the data retrieval engine 110 can query the electronic medical record databases 108 for data relevant to a patient, e.g., by way of an API made available by the electronic medical record databases 108.

The data retrieval engine 110 can query the electronic medical record databases 108 to retrieve any available data characterizing the patient that satisfies one or more predefined criteria. For instance, the data retrieval engine 110 can query the electronic medical record databases 108 to obtain any patient medical data of a type that is specified by one or more wildcard fields in the selected clinical note template 106. As another example, the data retrieval engine 110 can query the electronic medical record databases 108 to obtain a predefined number (e.g., one or two) of most recent clinical notes for the patient. As another example, the data retrieval engine 110 can query the electronic medical record databases 108 to obtain any sensor data generated by one or more sensors for the patient within a threshold duration of time prior to the current time, e.g., one minute, or one hour, or one day.

In some cases, the data retrieval engine 110 can determine that one or more sensors are generating real-time sensor data characterizing the current physiological state of the patient. For each sensor, the data retrieval engine 110 can transmit a request for recent sensor data generated by the sensor, thereby causing the sensor to transmit the requested sensor data to the data retrieval engine 110, e.g., by way of an appropriate data communications network. The data retrieval engine 110 can then include the sensor data obtained from the one or more sensors in the set of patient data 112 characterizing the patient, i.e., in addition to the electronic medical record data obtained by querying the electronic medical record databases.

The data processing engine 114 is configured to process: (i) the clinical note template 106, and (ii) the patient data 112 for the patient, to generate a model input 116 to the generative machine learning model 118. As part of generating the model input 116 to the generative machine learning model 118, the data processing engine 114 can process the patient data 112 to identify one or more medical classification codes that apply to the patient, and then include the applicable medical classification codes in the model input 116. The data processing engine 114 can also process sensor data included in the patient data 112 to derive one or more sensor data features, and then include the derived sensor data features in the model input 116 to the generative machine learning model. The data processing engine 114 can also identify and resolve any inconsistencies in the patient data 112, e.g., by prompting a user of the system 100 to select among multiple (possibly conflicting) entries for each of one or more fields in the electronic medical record data for the patient. An example process for processing patient data 112 for a patient to generate a model input to the generative machine learning model 118 is described in more detail below with reference to FIG. 3.

The generative machine learning model 118 is configured to process the model input 116, in accordance with values of a set of generative machine learning model parameters, to generate a model output that defines the clinical note 120 for the patient.

The generative machine learning model 118 can be any appropriate machine learning model that, when conditioned on a model input that includes a clinical note template 106 and patient data 112 for a patient, can generate samples from a space of possible model outputs in accordance with an underlying probability distribution over the space of possible model outputs. (The underlying probability distribution over the space of possible model outputs can be implicitly generated and represented by the generative machine learning model). The space of possible model outputs is the space of possible sequences of text, including sequences of text that define clinical notes for patients.

The generative machine learning model 118 can have any appropriate machine learning model architecture that enables the generative machine learning model 118 to perform its described functions. For instance, the generative machine learning model 118 can be implemented as a neural network with any appropriate neural network architecture, in particular, including any appropriate types of neural network layers (e.g., attention layers, fully connected layers, convolutional layers, pooling layers, and so forth) in any appropriate number (e.g., 5 layers, or 10 layers, or 50 layers) and connected in any appropriate configuration (e.g., as a directed graph of layers). In a particular example, the generative machine learning model 118 can be implemented with the Transformer architecture described with reference to: "Attention is all you need," Vaswani et al., arXiv: 1706.03762v7, 2 Aug. 2023.

The system 100 can train the generative machine learning model 118 by a machine learning training technique to perform a language modeling task on a set of training examples. Each training example can include a sequence of tokens defining a piece of text, where each token is drawn from a set of tokens that includes one or more of: characters, numbers, word pieces, words, and so forth. Training the generative machine learning model 118 on the training example to perform the language modeling task can include, for each of one or more positions in the sequence of tokens of the training example, training the generative machine learning model to predict the token that occupies the position based on the tokens that occupy preceding positions in the sequence of tokens. That is, the language modeling task can be a next token prediction task.

An example process for generating a clinical note using a generative machine learning model implemented as an autoregressive neural network is described with reference to FIG. 6. An example process for training a generative machine learning model implemented as a neural network to perform a language modeling task is described with reference to FIG. 7.

FIG. 2 is a flow diagram of an example process 200 for generating a clinical note for a patient. For convenience, the process 200 will be described as being performed by a system of one or more computers located in one or more locations. For example, a clinical note generation system, e.g., the clinical note generation system 100 of FIG. 1, appropriately programmed in accordance with this specification, can perform the process 200.

The system determines that a criterion for generating a new clinical note for the patient has been satisfied (202).

For instance, the system can determine that a criterion for generating a new clinical note for the patient has been satisfied when a user interacts with a graphical user interface made available by the system to request the generation of a new clinical note, as described above with reference to FIG. 1.

As another example, the system can perform continuous and automated monitoring of sensor data characterizing the physiological state of the patient, and can determine that a criterion for generating a new clinical note for the patient has been satisfied based on the monitoring of the sensor data. An example process for determining whether a criterion for generating a new clinical note for the patient has been satisfied based on automated and continuous monitoring of sensor data is described with reference to FIG. 4.

The system obtains a clinical note template that defines a format of a clinical note for the patient (204). The clinical note template defines a standardized framework for documenting healthcare services provided to a patient, and includes a sequence of text with one or more "wildcard fields" that are each designated to be replaced with a corresponding type of information related to the patient. A few specific examples of possible clinical note templates are described above with reference to FIG. 1.

The system can obtain the clinical note template from a predefined set of clinical note templates. The system can enable a user to select a clinical note template from the set of clinical note templates, e.g., by way of a user interface, or can select an appropriate clinical note template from the set of clinical note templates in an automated fashion, as described above with reference to FIG. 1.

The system automatically queries one or more electronic medical record databases to obtain a set of electronic medical record data for the patient (206).

Optionally, the system can additionally obtain sensor data that is generated by one or more sensors that are located on or in proximity to the patient and that characterize the physiological state of the patient (208). The system can obtain sensor data generated by any appropriate type of sensor. A few examples of sensor data that can be obtained by the system are described next.

In one example, the patient is a pregnant patient, and the system can obtain fetal heart rate sensor data generated by a fetal heart rate sensor. The fetal heart rate sensor data can be represented as a waveform that defines, at each time point in a sequence of time points, the heart rate of a fetus of the pregnant patient at the time point. The one or more time points can be separated by any appropriate interval, e.g., 3 seconds, 5 seconds, or 10 seconds, and can cover any appropriate duration of time, e.g., 1 minute, or 2 minutes, or 5 minutes. Fetal heart rate data can be generated, e.g., by external monitors (e.g., that use ultrasound to track the fetal heart rate), or internal monitors (e.g., that use a fetal scalp electrode attached to the scalp of the fetus). In some cases, fetal heart rate data can be generated by a non-stress test (NST) device.

In another example, the patient is a pregnant patient, and the system can obtain dilation sensor data generated by a dilation sensor. The dilation sensor data can be represented as a waveform that defines, at each time point in a sequence of time points, the amount of dilation of the cervix of the patient at the time point. The one or more time points can be separated by any appropriate interval, e.g., 3 seconds, 5 seconds, or 10 seconds, and can cover any appropriate duration of time, e.g., 1 minute, or 2 minutes, or 5 minutes.

In another example, the system can obtain drug dosage sensor data generated by a sensor such as a flow sensor that is integrated into an intravenous (IV) infusion system and that measures the rate at which the drug solution flows through the IV line. The drug dosage sensor data can be represented as a waveform that defines, at each time point in a sequence of time points, the amount of the drug administered to the patient at the time point. The one or more time points can be separated by any appropriate interval, e.g., 3 seconds, 5 seconds, or 10 seconds, and can cover any appropriate duration of time, e.g., 1 minute, or 2 minutes, or 5 minutes.

In another example, the system can obtain vital sign sensor data that is generated by a vital sign sensor and that characterizes one or more vital signs of the patient, e.g., body temperature, pulse (heart rate), respiratory rate, blood pressure, or oxygen saturation (SpO2, e.g., as measured by a pulse oximeter). The vital sign sensor data can be represented as a waveform that defines, at each time point in a sequence of time points, a measurement of the vital sign of the patient at the time point. The one or more time points can be separated by any appropriate interval, e.g., 3 seconds, 5 seconds, or 10 seconds, and can cover any appropriate duration of time, e.g., 1 minute, or 2 minutes, or 5 minutes.

In another example, the system can obtain capnography sensor data generated by a capnography sensor, e.g., that monitors the concentration of carbon dioxide in air exhaled by the patient.

In another example, the system can obtain electrocardiogram (ECG) sensor data generated by an ECG sensor, e.g., that tracks the electrical activity of the heart to detect arrhythmias or other cardiac issues.

In another example, the system can obtain anesthesia depth sensor data generated by an anesthesia depth sensor, e.g., that measures brain activity in the patient and can be used to ensure that the patient remains at the appropriate depth of anesthesia throughout a procedure.

In another example, the system can obtain pressure sensor data generated by a pressure sensor that can be used to detect early signs of pressure ulcers by monitoring pressure points and skin integrity, particularly in bedridden patients.

In another example, the system can obtain glucose measurement data generated by a glucose measurement sensor that measures glucose levels in the blood of the patient.

In another example, the patient is a pregnant patient, and the system can obtain sensor data measuring: the frequency and strength of uterine contractions during labor, e.g., using a tocometer; or the pressure inside the uterus, e.g., using an intrauterine pressure catheter (IUPC).

Optionally, the system obtains a user input that comprises textual notes characterizing the patient and/or healthcare services provided to the patient (210). For instance, the system can prompt the user to enter free form textual notes by way of a textbox in a user interface made available by the system on a user device of the user. The user can be, e.g., a healthcare provider for the patient.

The system generates a model input to the generative machine learning model based at least in part on: (i) the clinical note template, and (ii) the set of electronic medical record data for the patient (212). Optionally, the system also generates the model input to the generative machine learning model based on sensor data characterizing the current physiological state of the subject, e.g., as obtained at step 208, the free form textual notes provided by the user, e.g., as obtained at step 210, or both. An example process for generating the model input to the generative machine learning model is described in detail with reference to FIG. 3.

The system processes the model input using the generative machine learning model and in accordance with values of a set of generative machine learning model parameters to generate a model output that defines the clinical note for the patient (214). An example process for generating a clinical note for a patient using a generative machine learning model that is implemented as an autoregressive neural network is described with reference to FIG. 6.

The system outputs the clinical note generated by the generative machine learning model (216). In some cases, the system presents the clinical note to the user, e.g., by way of a user interface made available by the system on a user device, and prompts the user to confirm whether the clinical note is acceptable.

If the user indicates that the clinical note is not acceptable, e.g., by way of an appropriate interaction with the user interface, then the system can prompt the user to modify the clinical note. For instance, the system can enable the user to directly edit the clinical note using text editing functionality, e.g., that allows a user to add or delete text from the clinical note. As another example, the system can prompt the user to provide a free form textual input describing how the clinical note should be modified. The system can then update the clinical note using the textual input from the user describing how the clinical note should be modified and the generative machine learning model. An example process for adaptively updating the clinical note based on user feedback using the generative machine learning model is described with reference to FIG. 5.

If the user indicates that the clinical note is acceptable, then the system can store the clinical note in an electronic medical record associated with the patient.

Optionally, as an alternative to or in combination with storing the clinical note in the electronic medical record associated with the patient, the system can provide the clinical note for presentation on a display, e.g., that is included in a device (e.g., a tablet), e.g., that is mounted by the bedside of the patient.

Figure 3:
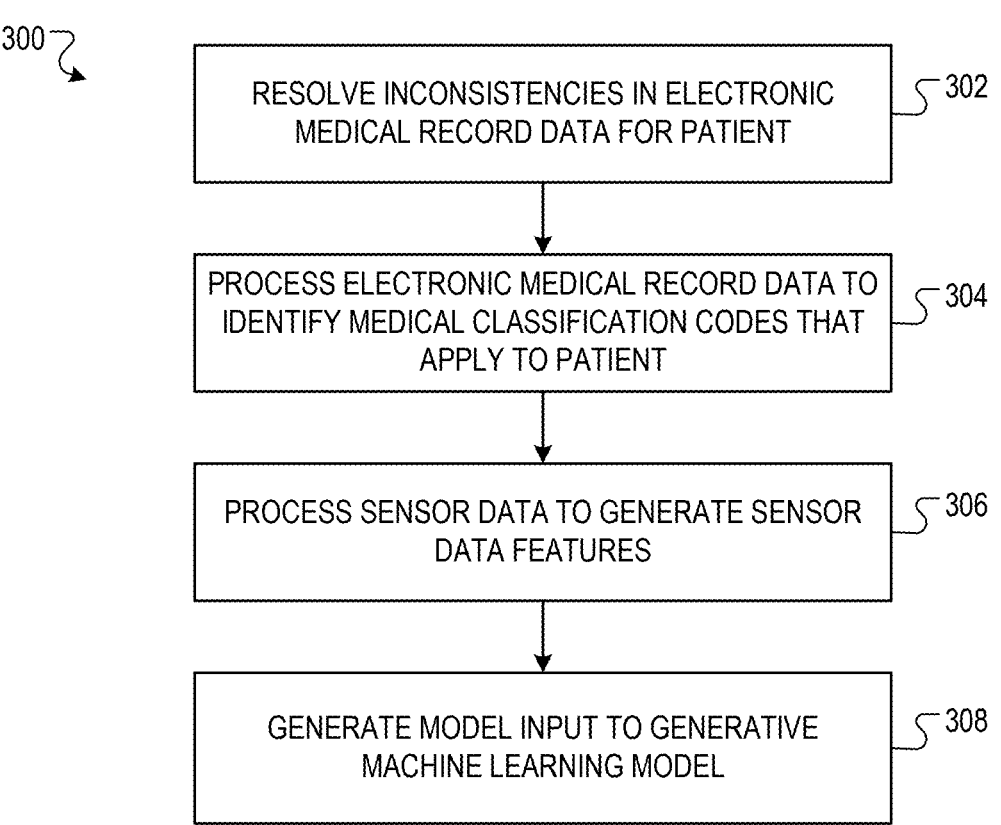
FIG. 3 is a flow diagram of an example process for generating a model input to a generative machine learning model that processes the model input to generate a clinical note for a patient.

FIG. 3 is a flow diagram of an example process 300 for generating a model input to a generative machine learning model that processes the model input to generate a clinical note for a patient. For convenience, the process 300 will be described as being performed by a system of one or more computers located in one or more locations. For example, a clinical note generation system, e.g., the clinical note generation system 100 of FIG. 1, appropriately programmed in accordance with this specification, can perform the process 300.

The system resolves any inconsistencies in the electronic medical record data obtained for the patient by querying the one or more electronic medical record databases (302). More specifically, the system can detect an inconsistency in the electronic medical record data for the patient by determining that the electronic medical record data includes multiple distinct (different) entries for a single field. A "field" can refer to a specific data element or attribute within the electronic medical record data for the patient that stores a particular piece of information about the patient. Examples of fields in the electronic medical record data can include, e.g., age, gender, body mass index, name, and so forth.

In response to determining that an inconsistency exists for a field in the electronic medical record data for the patient, the system can provide a representation of the multiple distinct entries for the field to a user by way of a user interface, and then prompt the user to select one of the distinct entries for the field. The system can receive selection data from the user, e.g., by way of an appropriate user interaction with the user interface, that selects one of the multiple distinct entries for the field as the entry to be used for generating the clinical note. The system can then include the selected entry for the field in the user input to the generative machine learning model, and discard the other entries for the field.

The system processes the electronic medical record data for the patient to classify, for each medical classification code in a predefined set of possible medical classification codes, whether the medical classification code applies to the patient (304). The set of medical classification codes can include any appropriate number of medical classification codes, e.g., at least 100, or at least 500, or at least 1000 medical classification codes. Each medical classification code in the set of possible medical classification codes can characterize a respective physiological state of the patient, medical condition of the patient (e.g., diagnoses of diseases, disorders, and injuries, such as diabetes, hypertension, fractures, and so forth), procedures and treatments provided to the patient (e.g., surgical procedures, diagnostic tests, therapeutic interventions, and so forth), clinical manifestations and symptoms observed in the patient (e.g., fever, pain, fatigue, and so forth), complications and comorbidities of the patient (e.g., secondary conditions or complications that arise during the course of treatment for primary conditions), and so forth.

For each medical classification code in the set of possible medical classification codes, the system can determine whether the medical classification code applies to the patient by evaluating whether the set of electronic medical record data for the patient satisfies one or more criteria associated with the medical classification code. Each criterion associated with a medical classification code can define that the medical classification code applies to the patient if a specified combination of one or more fields in the electronic medical record data for the patient have defined values. For at least some of the medical classification codes, the criteria associated with the evaluation of whether the medical classification code applies to the patient involves assessing whether multiple fields in the electronic medical record data for the patient have respective defined values.

Examples of medical classification codes can include, e.g., International Classification of Diseases, $10^{th}$ Revision (ICD-10) codes, Current Procedural Terminology (CPT) codes, Fast Healthcare Interoperability Resources (FHIR) standards, and Health Level Seven (HL7) codes. An example of a particular medical classification code is "obstetric care including antepartum care, cesarean delivery, and postpartum care." In order to evaluate whether this medical classification code applies to the patient, the system can automatically extract and assess multiple fields from the electronic medical record data for the patient, including fields relating to antepartum care, cesarean delivery, and postpartum care.

The system processes sensor data characterizing the physiological state of the patient to generate one or more features of the sensor data (306). The sensor data can be generated by any of a variety of possible sensors, e.g., fetal heart rate sensors, dilation sensors, drug dosage sensors, vital signs sensors, and so forth. The sensor data generated by each sensor can be represented as an ordered collection of one or more numerical values, e.g., a vector, matrix, or other tensor of numerical values, e.g., defining a waveform that defines a respective measurement value generated by the sensor for each time point in a sequence of time points.

In some implementations, the system can generate features of the sensor data by applying an appropriate aggregation operations to the sensor data, e.g., a minimum operation, or a maximum operation, or an averaging operation, or a summation operation, and so forth. Optionally, the system can perform signal processing operations that involve applying one or more transformation operations to the sensor data as part of generating the features of the sensor data, e.g., Fourier transform operations, wavelet transform operations, filtering operations (e.g., low pass, high pass, band pass, or band stop filtering operations), spectral decomposition operations, autocorrelation operations, and so forth.

In some implementations, the system can generate features of the sensor data by processing the sensor data using a classification machine learning model that is configured to generate a classification of the sensor data into a class from a set of possible classes. The classification machine learning model can be configured to perform any appropriate classification task, e.g., classifying whether the patient is in a healthy state or an unhealthy state, or classifying whether the patient is in a normal state or an abnormal state, or classifying an urgency with which the patient should be provided medical treatment (e.g., into classes including a low urgency class and a high urgency class), or classifying whether contraction patterns of the patient are normal or abnormal, or classifying the stage of labor of the patient, or classifying whether labor is likely to start within a predefined duration of time, and so forth.

The classification machine learning model can be implemented as any appropriate type of machine learning model, e.g., a neural network, or a decision tree, or a random forest, or a support vector machine, or a linear regression model, and so forth. Further, the classification machine learning model can have any appropriate machine learning model architecture that enables the classification machine learning model to perform its described functions. For instance, for a classification machine learning model implemented as a neural network, the classification machine learning model can include any appropriate types of neural network layers (e.g., attention layers, fully connected layers, convolutional layers, pooling layers, and so forth) in any appropriate number (e.g., 5 layers, or 10 layers, or 50 layers) and connected in any appropriate configuration (e.g., as a directed graph of layers).

The system can train the classification machine learning model on a set of training examples using a machine learning training technique to optimize an objective function. More specifically, each training example in the set of training examples can include: (i) a training input that is based on sensor data characterizing a training patient, and (ii) a target model output of the classification machine learning model for the training input. The objective function can measure, for each training example, a discrepancy between: (i) the target model output included in the training example, and (ii) a predicted model output generated by the classification machine learning model by processing the training input of the training example. The objective function can be, e.g., a cross-entropy objective function or a hinge loss objective function. The machine learning training technique can be any training technique appropriate for training the classification machine learning model, e.g., in implementations where the classification machine learning model is implemented as a neural network the system can use a stochastic gradient descent training technique.

The system generates the model input to the generative machine learning model based on the clinical note template and patient data including one or more of: (i) the electronic medical record data for the patient, (ii) medical classification codes that apply to the patient (as generated at step 304), or (iii) features of the sensor data characterizing the physiological state of the patient (as generated at step 306) (308). For instance, the system can generate the model input to the generative machine learning model by serializing and concatenating the clinical note template and the patient data into a single sequence of tokens, where each token is drawn from a set of tokens that includes one or more of: characters, numbers, word pieces, words, and so forth.

Figure 4:
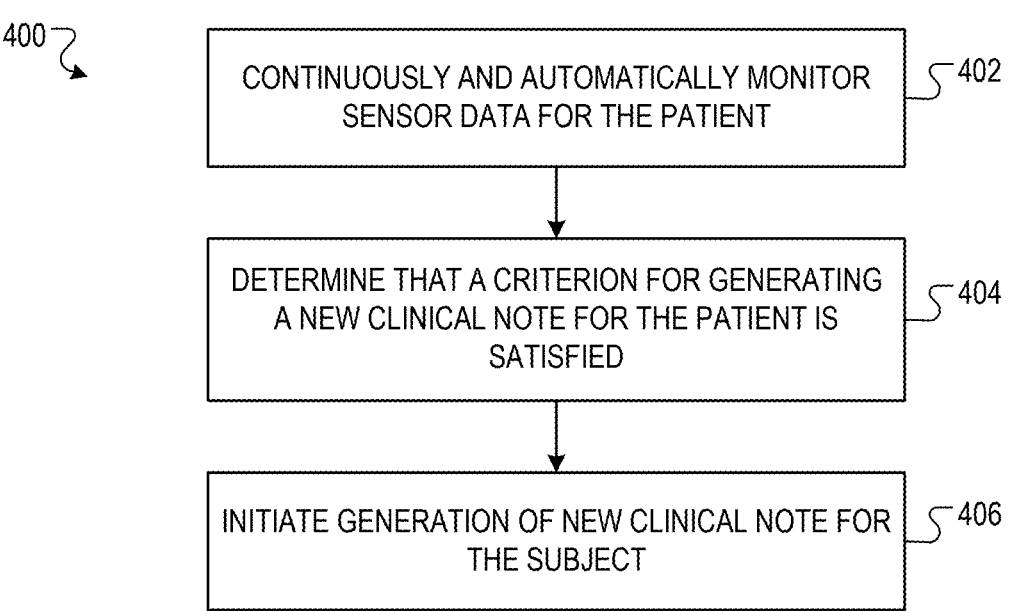
FIG. 4 is a flow diagram of an example process for determining whether a criterion for generating a new clinical note for a patient has been satisfied based on automated and continuous monitoring of sensor data.

FIG. 4 is a flow diagram of an example process 400 for determining whether a criterion for generating a new clinical note for a patient has been satisfied based on automated and continuous monitoring of sensor data. For convenience, the process 400 will be described as being performed by a system of one or more computers located in one or more locations. For example, a clinical note generation system, e.g., the clinical note generation system 100 of FIG. 1, appropriately programmed in accordance with this specification, can perform the process 400.

The system performs continuous and automated monitoring of real-time sensor data that is generated by one or more sensors located on or in proximity to the patient and that characterize a current physiological state of the patient (402). More specifically, for each of one or more sensors, the system can continuously obtain real-time sensor data generated by the sensor, e.g., on a regular a cadence, e.g., every 5 seconds, or every 1 minute, or every 10 minutes. The system can obtain current sensor data generated by the sensor, e.g., by querying an electronic medical record that stores real-time sensor data generated by the sensor, or by directly querying the sensor device by way of an interface made available by the sensor device.

The system determines, based on the continuous and automated monitoring of the real-time sensor data, whether a criterion for generating a new clinical note for the patient has been satisfied (404). For instance, each time the system obtains current sensor data from a sensor (as described at step 402), the system can process the current sensor data, e.g., using signal processing operations and/or a classification machine learning model, to generate one or more features of the sensor data. (Example techniques for generating features of sensor data are described with reference to step 306 of FIG. 3). The system can then determine whether a criterion for generating a new clinical note for the patient has been satisfied based on the features of the sensor data.

For example, the system can process the sensor data using a classification machine learning model to classify the sensor data, and the system can determine that a criterion for generating a new clinical note is satisfied if the sensor data is classified into one or more designated classes, e.g., classes indicating that the patient is in an unhealthy or abnormal state.

As another example, the system can process the sensor data using signal processing and aggregation operations to generate a summary statistic for the sensor data (e.g., a maximum value of the sensor data, or a minimum value of the sensor data, or a measure of central tendency of the sensor data). The system can then determine that a criterion for generating a new clinical note is satisfied if the summary statistic satisfies (e.g., exceeds or falls below) a predefined threshold.

As another example, the system can determine whether a criterion for generating a new clinical note is satisfied based on a comparison of: (i) a current value of a feature of the sensor data, and (ii) a previous value of the feature of the sensor data. For instance, for a feature that assumes values in a continuous range of possible values, the system can determine that a criterion for generating a new clinical note is satisfied if the current value of the feature differs from the previous value of the feature by at least a predefined threshold amount. As another example, for a feature that classifies the sensor data into a set of possible classes, the system can determine that a criterion for generating a new clinical note is satisfied if the current classification of the sensor data is different than the previous classification of the sensor data.

In response to determining that a criterion for generating a new clinical note for the patient is satisfied, the system initiates the generation of a new clinical note, e.g., by initiating the process described with reference to FIG. 2.

FIG. 5 is a flow diagram of an example process 500 for adaptively updating a clinical note generated by a generative machine learning model based on user feedback. For convenience, the process 500 will be described as being performed by a system of one or more computers located in one or more locations. For example, a clinical note generation system, e.g., the clinical note generation system 100 of FIG. 1, appropriately programmed in accordance with this specification, can perform the process 500.

After presenting a clinical note generated by the generative machine learning model to a user (e.g., by the process described with reference to FIG. 2), the system receives a request to modify the clinical note from the user (502). For instance, the system can receive a free form textual input from the user that defines a request to modify the clinical note according to criteria defined in the user input (e.g., "actually the gender of the baby was male," or "add that shoulder dystocia occurred during the birth and was resolved using the McRoberts maneuver").

The system generates a new model input to the generative machine learning model that includes at least: (i) the original clinical note, i.e., that was previously presented to the user, and (ii) data defining the request from the user to modify the original clinical note (504). For instance, the system can generate the new model input by concatenating respective sequences of text including the original clinical note and free form textual data provided by the user that defines the request to modify the original clinical note. Optionally the system can include additional data in the new model input to the generative machine learning model, e.g., including one or more of: (i) the electronic medical record data for the patient, (ii) medical classification codes that apply to the patient, or (iii) features of the sensor data characterizing the physiological state of the patient.

The system processes the new model input using the generative machine learning model and in accordance with values of a set of generative machine learning model parameters to generate an updated clinical note for the patient that reflects the request to modify the original clinical note for the patient (506). An example process for processing a model input using a generative machine learning model that is implemented as an autoregressive neural network to generate a clinical note (e.g., an updated clinical note) is described with reference to FIG. 6.

The system outputs the updated clinical note, e.g., by providing the updated clinical note for presentation to the user on a display of a user device (508). The system can prompt the user to confirm whether the updated clinical note is acceptable. If the user indicates that the updated clinical note is not acceptable, the system can prompt the user to modify the updated clinical note, and can perform another iteration of the steps of the process 500. If the user indicates that the updated clinical note is acceptable, the system can store the updated clinical note in an electronic medical record associated with the patient.

Figure 6:
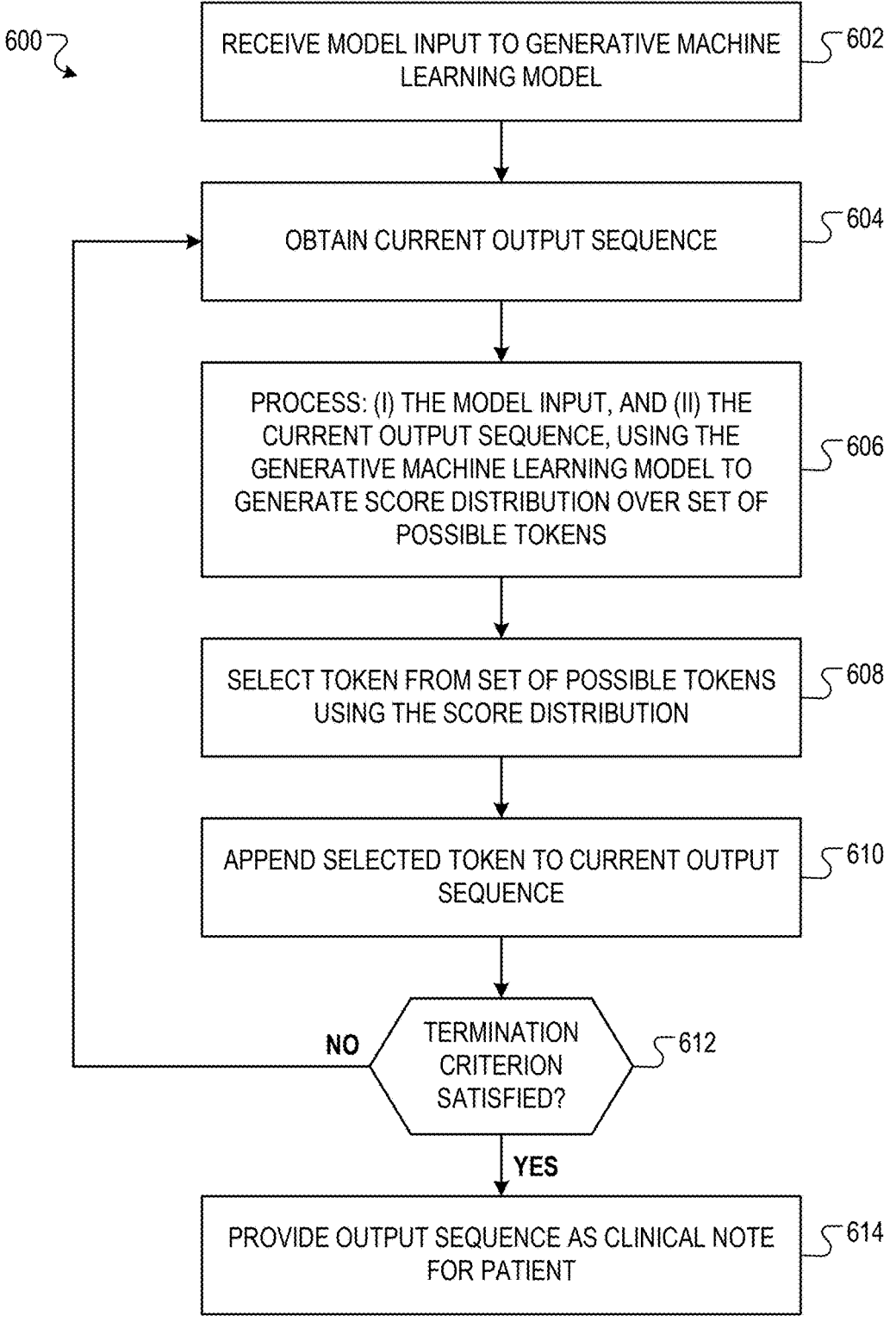
FIG. 6 is a flow diagram of an example process for generating a clinical note using a generative machine learning model implemented as an autoregressive neural network.

FIG. 6 is a flow diagram of an example process 600 for generating a clinical note using a generative machine learning model implemented as an autoregressive neural network. For convenience, the process 600 will be described as being performed by a system of one or more computers located in one or more locations. For example, a clinical note generation system, e.g., the clinical note generation system 100 of FIG. 1, appropriately programmed in accordance with this specification, can perform the process 600.

The system receives a model input to the generative machine learning model (602). The model input can include: (i) a clinical note template, and (ii) a set of electronic medical record data for the patient. Optionally, the model input to generative machine learning model can additionally include one or more of: a set of medical classification codes that apply to the patient, or features of sensor data characterizing a physiological state of the patient, or both. The model input to the generative machine learning model can be represented as a sequence of input tokens, where each token is drawn from a set of tokens that includes one or more of: characters, numbers, word pieces, words, and so forth.

The system uses the generative machine learning model to generate a sequence of output tokens that collectively define the clinical note for the patient one token at a time, starting from a first position in the sequence of output tokens. The generative machine learning model generates the sequence of output tokens autoregressively, i.e., so that the token selected for each position in the output sequence of tokens depends on the tokens generated for any preceding positions in the output sequence of tokens (and on the sequence of input tokens defining the model input to generate machine learning model).

Steps 604-612, which are described next, illustrate an example of how the system can generate a token at a particular position in the sequence of output tokens. The system can iteratively perform the steps 604-612 for each token in the sequence of output tokens, one position at a time and starting from the first position in the sequence of output tokens. For convenience, steps 604-612 are described with reference to a "current" position in the sequence of output tokens.

The system obtains a current sequence of output tokens (604). The current sequence of output tokens includes a respective token for each position prior to the current position in the sequence of output tokens.

The system processes: (i) the sequence of input tokens included in the model input, and (ii) the current sequence of output tokens, using the generative machine learning model and in accordance with values of a set of generative machine learning model parameters, to generate a score distribution over a set of possible tokens (606). The set of possible tokens can include one or more of: characters, numbers, word pieces, words, and so forth. The score distribution over the set of possible tokens can assign a respective score, e.g., represented as a numerical value, to each token in the set of possible tokens. The score for a token can define a likelihood that the token occupies the current position in the sequence of output tokens.

The system selects a token for the current position in the sequence of output tokens in accordance with the score distribution over the set of possible tokens (608). For instance, the system can select a token that has a highest score under the score distribution over the set of possible tokens. As another example, the system can stochastically sample a token from a probability distribution over the set of possible tokens, e.g., that is generated by applying a softmax function to the score distribution over the set of possible tokens.

The system appends the token selected for the current position in the sequence of output tokens to the current sequence of output tokens, i.e., such that the selected token occupies the current position in the sequence of output tokens (610).

The system determines whether a termination criterion has been satisfied (612). For instance, the termination criterion can be that the token selected for the current position in the sequence of output tokens is a predefined "end-of-sequence" (EOS) token. As another example, the termination criterion can be that the current sequence of output tokens has reached a predefined maximum length.

In response to determining that a termination criterion is not satisfied, the system can return to step 604 and proceed to select a token to occupy the next position in the sequence of output tokens.

In response to determining that a termination criterion has been satisfied, the system can provide the sequence of output tokens as the clinical note for the patient (614).

Figure 7:
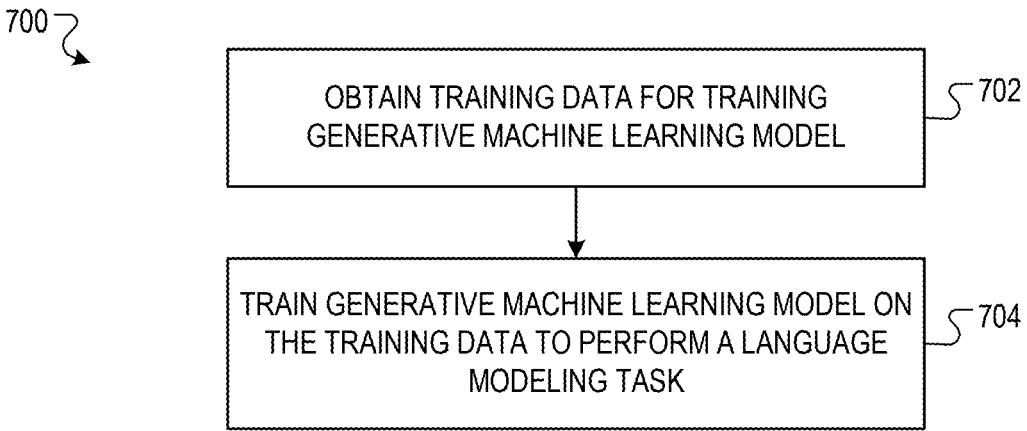
FIG. 7 is a flow diagram of an example process for training a generative machine learning model implemented as a neural network to perform a language modeling task.

FIG. 7 is a flow diagram of an example process 700 for training a generative machine learning model implemented as a neural network to perform a language modeling task.

For convenience, the process 700 will be described as being performed by a system of one or more computers located in one or more locations. For example, a clinical note generation system, e.g., the clinical note generation system 100 of FIG. 1, appropriately programmed in accordance with this specification, can perform the process 700.

The system obtains a set of training data for training the generative machine learning model (702). The set of training data includes a set of training examples, where each training example includes a sequence of tokens defining a piece of text. The set of training data can include multiple training examples that correspond to clinical notes, e.g., operative notes, delivery notes, or progress notes. (Any clinical notes included the training data for training the generative machine learning model are anonymized to remove patient identifiers and otherwise compliant with the Health Insurance Portability and Accountability Act (HIPAA)).

The system trains the generative machine learning model on the set of training data to perform a language modeling task (704). More specifically, to train the generative machine learning model on a training example in the training data, the system can select a target position (which is after the first position) in the sequence of tokens included in the training example. The system can process a subsequence of the sequence of tokens that precedes the target position using the generative machine learning model to generate a score distribution over a set of possible tokens. The system can then train the generative machine learning model to optimize an objective function (e.g., a cross-entropy objective function) that measures a discrepancy between: (i) the token that occupies the target position in the sequence of output tokens, and (ii) the score distribution over the set of possible tokens that is generated by the generative machine learning model. For instance, the system can determine gradients of the objective function with respect to the set of generative machine learning model parameters, e.g., using backpropagation, and then use the gradients to adjust the current values of the set of generative machine learning model parameters, e.g., in accordance with the update rule of an appropriate gradient descent optimization procedure, e.g., RMSprop or Adam. That is, the system can train the generative machine learning model to perform a next token prediction task, i.e., by predicting the token occupying the target position in the sequence of tokens based on the tokens at preceding positions in the sequence of tokens.

This specification uses the term "configured" in connection with systems and computer program components. For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non-transitory storage medium for execution by, or to control the operation of, data processing apparatus. The computer storage medium can be a machine-readable storage device, a machine-readable storage substrate, a random or serial access memory device, or a combination of one or more of them. Alternatively or in addition, the program instructions can be encoded on an artificially-generated propagated signal, e.g., a machine-generated electrical, optical, or electromagnetic signal, that is generated to encode information for transmission to suitable receiver apparatus for execution by a data processing apparatus.

The term "data processing apparatus" refers to data processing hardware and encompasses all kinds of apparatus, devices, and machines for processing data, including by way of example a programmable processor, a computer, or multiple processors or computers. The apparatus can also be, or further include, special purpose logic circuitry, e.g., an FPGA (field programmable gate array) or an ASIC (application-specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program, which may also be referred to or described as a program, software, a software application, an app, a module, a software module, a script, or code, can be written in any form of programming language, including compiled or interpreted languages, or declarative or procedural languages; and it can be deployed in any form, including as a stand-alone program or as a module, component, subroutine, or other unit suitable for use in a computing environment. A program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a data communication network.

In this specification the term "engine" is used broadly to refer to a software-based system, subsystem, or process that is programmed to perform one or more specific functions. Generally, an engine will be implemented as one or more software modules or components, installed on one or more computers in one or more locations. In some cases, one or more computers will be dedicated to a particular engine; in other cases, multiple engines can be installed and running on the same computer or computers.

The processes and logic flows described in this specification can be performed by one or more programmable computers executing one or more computer programs to perform functions by operating on input data and generating output. The processes and logic flows can also be performed by special purpose logic circuitry, e.g., an FPGA or an ASIC, or by a combination of special purpose logic circuitry and one or more programmed computers.

Computers suitable for the execution of a computer program can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. The central processing unit and the memory can be supplemented by, or incorporated in, special purpose logic circuitry. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer-readable media suitable for storing computer program instructions and data include all forms of nonvolatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser. Also, a computer can interact with a user by sending text messages or other forms of message to a personal device, e.g., a smartphone that is running a messaging application, and receiving responsive messages from the user in return.

Data processing apparatus for implementing machine learning models can also include, for example, special-purpose hardware accelerator units for processing common and compute-intensive parts of machine learning training or production, i.e., inference, workloads.

Machine learning models can be implemented and deployed using a machine learning framework, e.g., a TensorFlow framework, or a Jax framework.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface, a web browser, or an app through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML page, to a user device, e.g., for purposes of displaying data to and receiving user input from a user interacting with the device, which acts as a client. Data generated at the user device, e.g., a result of the user interaction, can be received at the server from the device.

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially be claimed as such, one or more features from a claimed combination can in some cases be excised from the combination, and the claimed combination may be directed to a subcombination or variation of a subcombination.

Similarly, while operations are depicted in the drawings and recited in the claims in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

What is claimed is:

1. A method performed by one or more computers, the method comprising:

obtaining a clinical note template that defines a format of a clinical note for a patient, comprising:

presenting, to a user and on a display of a user device, a plurality of possible clinical note templates, wherein each of the plurality of possible clinical note templates comprises a sequence of text with a plurality of wildcard fields, wherein each wildcard field is designated to be replaced with a corresponding type of information related to the patient; and receiving, from the user, a selection that identifies the clinical note template from among the plurality of possible clinical note templates;

wherein the clinical note template is a template for an operative note that describes a surgery performed on the patient or a template for a delivery note that describes a childbirth process for the patient;

automatically querying one or more electronic medical record databases to obtain a set of electronic medical record data for the patient;

automatically querying each of a plurality of sensors that are on or in proximity to the patient to obtain a waveform generated by the sensor that characterizes a physiological state of the patient, wherein the plurality of sensors comprise one or more of: a fetal heartrate sensor, or a dilation sensor, or a drug dosage sensor, or a capnography sensor, or an anesthesia depth sensor;

processing, for each of the plurality of sensors, the waveform generated by the sensor using a respective classification machine learning model;

generating a patient state classification based on the processed waveform, wherein the patient state classification classifies a state of the patient into a class from a set of classes;

generating a model input to a generative neural network, the generating the model input comprising serializing and concatenating: (i) the clinical note template, and (ii) patient data comprising the set of electronic medical record data for the patient and the patient state classifications generated by processing the waveforms generated by the plurality of sensors;

processing the model input using the generative neural network and in accordance with values of a set of generative neural network parameters to generate a model output that defines the clinical note for the patient, wherein the generative neural network has been trained by a machine learning training technique to perform a language modeling task;

wherein the model output that defines the clinical note for the patient comprises a sequence of textual tokens; and wherein processing the model input using the generative neural network and in accordance with values of the set of generative neural network parameters to generate the model output that defines the clinical note for the patient comprises, for each of a plurality of positions in the sequence of textual tokens of the clinical note:

processing: (i) the model input, and (ii) any textual tokens at preceding positions that precede the position in the sequence of textual tokens of the clinical note, using the generative neural network model to generate a score distribution over a set of possible textual tokens; and selecting a textual token to occupy the position in the sequence of textual tokens using the score distribution over the set of possible textual tokens;

receiving, by a user interface and from the user, a free-form textual query that defines a request to modify the clinical note for the patient;

generating a new model input to the generative neural network that comprises a concatenation of: (i) the clinical note for the patient, and (ii) the free-form textual query that defines the request to modify the clinical note for the patient;

processing the new model input using the generative neural network and in accordance with the values of the set of generative neural network parameters to generate a new clinical note for the patient that reflects the request to modify the clinical note for the patient; and outputting the new clinical note for the patient.

2. The method of claim 1, wherein generating the model input to the generative neural network comprises:

processing the set of electronic medical record data for the patient to classify, for each medical classification code in a predefined set of possible medical classification codes, whether the medical classification code applies to the patient;

identifying that one or more medical classification codes from the predefined set of possible medical classification codes apply to the patient; and in response, including the one or more medical classification codes that apply to the patient in the model input to the generative neural network.

3. The method of claim 2, wherein processing the set of electronic medical record data for the patient to classify, for each medical classification code in the predefined set of possible medical classification codes, where the medical classification code applies to the patient comprises, for each medical classification code in the predefined set of possible medical classification codes:

determining whether the medical classification code applies to the patient by evaluating whether the set of electronic medical record data for the patient satisfies one or more criteria associated with the medical classification code.

4. The method of claim 1, wherein the plurality of sensors comprise a fetal heart rate sensor which is configured to generate fetal heartrate data for one or more fetuses of the patient.

5. The method of claim 1, wherein the plurality of sensors comprise a dilation sensor which is configured to generate dilation data that defines an amount of dilation of a cervix of the patient.

6. The method of claim 1, wherein the plurality of sensors comprise a drug dosage sensor which is configured to generate sensor data characterizing an amount of a drug being administered to the patient.

7. The method of claim 1, wherein generating the model input to the generative neural network comprises:

determining, for one or more fields in the electronic medical record data for the patient, that the electronic medical record includes a plurality of distinct entries for the field; and providing, by a user interface, an option to select one of the plurality of distinct entries for the field; and receiving, from by way of the user interface, selection data that selects one of the plurality of distinct entries for the field; and including only the selected entry for the field in the model input to the generative neural network.

8. The method of claim 1, wherein outputting the clinical note for the patient comprises:

presenting the clinical note on a display of a device.

9. The method of claim 1, further comprising:

continuously and automatically monitoring sensor data generated by the plurality of sensors;

determining, based on the continuous and automated monitoring of the plurality of sensors, that a criterion for generating a clinical note for the patient has been satisfied; and in response, generating the clinical note for the patient.

10. The method of claim 9, wherein determining, based on the continuous and automated monitoring of the plurality of sensors, that the criterion for generating the clinical note for the patient has been satisfied comprises:

processing current sensor data for the patient to generate a current feature of the current sensor data;

determining that the criterion for generating the clinical note for the patient has been satisfied based on the current feature of the current sensor data.

11. The method of claim 1, wherein selecting a textual token to occupy the position in the sequence of textual tokens using the score distribution over the set of possible textual tokens comprises:

selecting a textual token having a highest score under the score distribution over the set of possible textual tokens as the textual token to occupy the position in the sequence of textual tokens.

12. The method of claim 1, wherein the set of electronic medical record data for the patient comprises one or more previous clinical notes for the patient.

13. A system comprising:

one or more computers; and one or more storage devices communicatively coupled to the one or more computers, wherein the one or more storage devices store instructions that, when executed by the one or more computers, cause the one or more computers to perform operations comprising:

obtaining a clinical note template that defines a format of a clinical note for a patient, comprising:

presenting, to a user and on a display of a user device, a plurality of possible clinical note templates, wherein each of the plurality of possible clinical note templates comprises a sequence of text with a plurality of wildcard fields, wherein each wildcard field is designated to be replaced with a corresponding type of information related to the patient; and receiving, from the user, a selection that identifies the clinical note template from among the plurality of possible clinical note templates;

wherein the clinical note template is a template for an operative note that describes a surgery performed on the patient or a template for a delivery note that describes a childbirth process for the patient;

automatically querying one or more electronic medical record databases to obtain a set of electronic medical record data for the patient;

automatically querying each of a plurality of sensors that are on or in proximity to the patient to obtain a waveform generated by the sensor that characterizes a physiological state of the patient, wherein the plurality of sensors comprise one or more of: a fetal heartrate sensor, or a dilation sensor, or a drug dosage sensor, or a capnography sensor, or an anesthesia depth sensor;

processing, for each of the plurality of sensors, the waveform generated by the sensor using a respective classification machine learning model;

generating a patient state classification based on the processed waveform, wherein the patient state classification classifies a state of the patient into a class from a set of classes;

generating a model input to a generative neural network, the generating the model input comprising serializing and concatenating: (i) the clinical note template, and (ii) patient data comprising the set of electronic medical record data for the patient and the patient state classifications generated by processing the waveforms generated by the plurality of sensors;

processing the model input using the generative neural network and in accordance with values of a set of generative neural network parameters to generate a model output that defines the clinical note for the patient, wherein the generative neural network has been trained by a machine learning training technique to perform a language modeling task;

wherein the model output that defines the clinical note for the patient comprises a sequence of textual tokens; and wherein processing the model input using the generative neural network and in accordance with values of the set of generative neural network parameters to generate the model output that defines the clinical note for the patient comprises, for each of a plurality of positions in the sequence of textual tokens of the clinical note:

processing: (i) the model input, and (ii) any textual tokens at preceding positions that precede the position in the sequence of textual tokens of the clinical note, using the generative neural network model to generate a score distribution over a set of possible textual tokens; and selecting a textual token to occupy the position in the sequence of textual tokens using the score distribution over the set of possible textual tokens;

receiving, by a user interface and from the user, a free-form textual query that defines a request to modify the clinical note for the patient;

generating a new model input to the generative neural network that comprises a concatenation of: (i) the clinical note for the patient, and (ii) the free-form textual query that defines the request to modify the clinical note for the patient;

processing the new model input using the generative neural network and in accordance with the values of the set of generative neural network parameters to generate a new clinical note for the patient that reflects the request to modify the clinical note for the patient; and outputting the new clinical note for the patient.

14. The system of claim 13, wherein generating the model input to the generative neural network comprises:

processing the set of electronic medical record data for the patient to classify, for each medical classification code in a predefined set of possible medical classification codes, whether the medical classification code applies to the patient;

identifying that one or more medical classification codes from the predefined set of possible medical classification codes apply to the patient; and in response, including the one or more medical classification codes that apply to the patient in the model input to the generative neural network.

15. The system of claim 14, wherein processing the set of electronic medical record data for the patient to classify, for each medical classification code in the predefined set of possible medical classification codes, where the medical classification code applies to the patient comprises, for each medical classification code in the predefined set of possible medical classification codes:

determining whether the medical classification code applies to the patient by evaluating whether the set of electronic medical record data for the patient satisfies one or more criteria associated with the medical classification code.

16. One or more non-transitory computer storage media storing instructions that when executed by one or more computers cause the one or more computers to perform operations comprising:

obtaining a clinical note template that defines a format of a clinical note for a patient, comprising:

presenting, to a user and on a display of a user device, a plurality of possible clinical note templates, wherein each of the plurality of possible clinical note templates comprises a sequence of text with a plurality of wildcard fields, wherein each wildcard field is designated to be replaced with a corresponding type of information related to the patient; and receiving, from the user, a selection that identifies the clinical note template from among the plurality of possible clinical note templates;

wherein the clinical note template is a template for an operative note that describes a surgery performed on the patient or a template for a delivery note that describes a childbirth process for the patient;

automatically querying one or more electronic medical record databases to obtain a set of electronic medical record data for the patient;

automatically querying each of a plurality of sensors that are on or in proximity to the patient to obtain a waveform generated by the sensor that characterizes a physiological state of the patient, wherein the plurality of sensors comprise one or more of: a fetal heartrate sensor, or a dilation sensor, or a drug dosage sensor, or a capnography sensor, or an anesthesia depth sensor;

processing, for each of the plurality of sensors, the waveform generated by the sensor using a respective classification machine learning model;

generating a patient state classification based on the processed waveform, wherein the patient state classification classifies a state of the patient into a class from a set of classes;

generating a model input to a generative neural network, the generating the model input comprising serializing and concatenating: (i) the clinical note template, and (ii) patient data comprising the set of electronic medical record data for the patient and the patient state classifications generated by processing the waveforms generated by the plurality of sensors;

processing the model input using the generative neural network and in accordance with values of a set of generative neural network parameters to generate a model output that defines the clinical note for the patient, wherein the generative neural network has been trained by a machine learning training technique to perform a language modeling task;

wherein the model output that defines the clinical note for the patient comprises a sequence of textual tokens; and wherein processing the model input using the generative neural network and in accordance with values of the set of generative neural network parameters to generate the model output that defines the clinical note for the patient comprises, for each of a plurality of positions in the sequence of textual tokens of the clinical note:

processing: (i) the model input, and (ii) any textual tokens at preceding positions that precede the position in the sequence of textual tokens of the clinical note, using the generative neural network model to generate a score distribution over a set of possible textual tokens; and selecting a textual token to occupy the position in the sequence of textual tokens using the score distribution over the set of possible textual tokens;

receiving, by a user interface and from the user, a free-form textual query that defines a request to modify the clinical note for the patient;

generating a new model input to the generative neural network that comprises a concatenation of: (i) the clinical note for the patient, and (ii) the free-form textual query that defines the request to modify the clinical note for the patient;

processing the new model input using the generative neural network and in accordance with the values of the set of generative neural network parameters to generate a new clinical note for the patient that reflects the request to modify the clinical note for the patient; and outputting the new clinical note for the patient.

17. The non-transitory computer storage media of claim 16, wherein generating the model input to the generative neural network comprises:

processing the set of electronic medical record data for the patient to classify, for each medical classification code in a predefined set of possible medical classification codes, whether the medical classification code applies to the patient;

identifying that one or more medical classification codes from the predefined set of possible medical classification codes apply to the patient; and in response, including the one or more medical classification codes that apply to the patient in the model input to the generative neural network.

18. The non-transitory computer storage media of claim 17, wherein processing the set of electronic medical record data for the patient to classify, for each medical classification code in the predefined set of possible medical classification codes, where the medical classification code applies to the patient comprises, for each medical classification code in the predefined set of possible medical classification codes:

determining whether the medical classification code applies to the patient by evaluating whether the set of electronic medical record data for the patient satisfies one or more criteria associated with the medical classification code.

19. The non-transitory computer storage media of claim 16, wherein the plurality of sensors comprise a fetal heart rate sensor which is configured to generate fetal heartrate data for one or more fetuses of the patient.

20. The non-transitory computer storage media of claim 16, wherein the plurality of sensors comprise a dilation sensor which is configured to generate dilation data that defines an amount of dilation of a cervix of the patient.

21. The non-transitory computer storage media of claim 16, wherein the plurality of sensors comprise a drug dosage sensor which is configured to generate sensor data characterizing an amount of a drug being administered to the patient.

22. The non-transitory computer storage media of claim 16, wherein generating the model input to the generative neural network comprises:

determining, for one or more fields in the electronic medical record data for the patient, that the electronic medical record includes a plurality of distinct entries for the field; and providing, by a user interface, an option to select one of the plurality of distinct entries for the field; and receiving, from by way of the user interface, selection data that selects one of the plurality of distinct entries for the field; and including only the selected entry for the field in the model input to the generative neural network.

23. The non-transitory computer storage media of claim 16, wherein selecting a textual token to occupy the position in the sequence of textual tokens using the score distribution over the set of possible textual tokens comprises:

selecting a textual token having a highest score under the score distribution over the set of possible textual tokens as the textual token to occupy the position in the sequence of textual tokens.

24. The non-transitory computer storage media of claim 16, wherein the set of electronic medical record data for the patient comprises one or more previous clinical notes for the patient.

* * * * *